United States Patent [19]

Furuoya et al.

[11] 4,436,671
[45] Mar. 13, 1984

[54] PROCESS FOR PRODUCING UNSATURATED ALIPHATIC DINITRILES

[75] Inventors: Itsuo Furuoya, Suita; Yuzuru Kitazawa, Hirakata, both of Japan

[73] Assignee: Takeda Chemical Industries, Limited, Osaka, Japan

[21] Appl. No.: 344,936

[22] Filed: Feb. 2, 1982

[30] Foreign Application Priority Data

Feb. 12, 1981 [JP] Japan .................. 56-19941

[51] Int. Cl.³ .......................................... C07C 120/14
[52] U.S. Cl. .............................................. 260/465.3
[58] Field of Search ................................... 260/465.3

[56] References Cited

U.S. PATENT DOCUMENTS

| 3,342,849 | 9/1967 | Brill et al. | 260/465.3 |
| 3,345,397 | 10/1967 | Finley | 260/465.3 |
| 3,859,326 | 1/1975 | Saito et al. | 260/465.3 |

FOREIGN PATENT DOCUMENTS 2244264 3/1973 Fed. Rep. of Germany .
1394207 5/1975 United Kingdom .

*Primary Examiner*—Joseph Paul Brust
*Attorney, Agent, or Firm*—Wenderoth, Lind & Ponack

[57] ABSTRACT

Unsaturated aliphatic dinitriles such as fumaronitrile and maleonitrile can be produced in high yields by ammoxidation of $C_4$ straight-chain hydrocarbons in the presence of a catalyst containing as active components:

[A] at least one kind of oxides of vanadium and tungsten, and

[B]
  (1) at least one kind of oxides of antimony, phosphorus and boron, and/or
  (2) at least one kind of oxides of chromium, nickel, aluminum and silicon.

7 Claims, No Drawings

PROCESS FOR PRODUCING UNSATURATED ALIPHATIC DINITRILES

The present invention relates to a process for producing unsaturated aliphatic dinitriles such as fumaronitrile and maleonitrile by the ammoxidation of straight-chain hydrocarbons of 4 carbon atoms.

As the methods of producing fumaronitrile and maleonitrile, there have been proposed, for example, (1) the process involving the dehydration of diamide of maleic acid or fumaric acid with phosphorus pentaoxide (U.S. Pat. No. 2,438,019), (2) the process comprising the reaction of diiodoethylene with copper cyanide (U.S. Pat. No. 2,399,349), (3) the process which comprises dimerization of acetonitrile by dehydrogenation in the presence of chlorine at elevated temperatures (Japanese Patent Publication No. 17965/1967), (4) the process involving the addition of hydrogen cyanide to cyanoacetylene (Japanese Published Unexamined Patent Application No. 111019/1975) and (5) the processes comprising the ammoxidation of benzene (West-German Patent Application OLS No. 2,128,753), cyclohexane (Japanese Published Unexamined Patent Application Nos. 11802 through 11807/1967), phenol (Japanese Published Unexamined Patent Application No. 15318/1978) and butadiene (West-German Patent Application OLS No. 2,244,264), and others.

However, these processes each have the problems; the processes (2) and (4) encounter difficulties in the procurement of the starting materials which are special, and (1) and (3) involve practical difficulties in controlling the reaction conditions which are too strict, while (5), with its low yields, lacks economy. And, at present, none of these has yet been actually established as an industrial production process. Circumstances being such as above, these nitriles can hardly be supplied to the market in sufficient amounts. Thus, some restriction has been inevitably imposed upon the use of these dinitriles as starting materials to be employed on an industrial scale although these have been recognized as useful compounds as starting materials for various medicines, industrial chemicals or polymers.

The present inventors, with a specific view to solving these problems, choose $C_4$ straight-chain hydrocarbons, particularly butane, butene, butadiene or their mixtures, as the readily available and lower-priced raw material, and have conducted extensive investigations on the development of a technology which permits the production in high yields of the unsaturated aliphatic dinitriles of fumaronitrile and maleonitrile by the reaction of these hydrocarbons with ammonia and molecular oxygen, namely an ammoxidation reaction.

As the catalyst for the ammoxidation of butadiene to produce unsaturated nitriles, there have been already proposed catalysts based on vanadium oxide/molybdenum oxide, molybdenum oxide/bismuth oxide/phosphorus oxide, or iron oxide/antimony oxide (West-German Patent Application OLS No. 2,244,264, Japanese Patent Publication No. 24294/1975). Nevertheless, the process affords fumaronitrile or maleonitrile in yields of no more than 5 mole% based on the supplied butadiene, and has the problem of lower yields.

In view of this, the present inventors conducted extensively the development on a catalyst system which is different from the above catalysts and is capable of ammoxidation of $C_4$ hydrocarbons as well. The development work led to the finding that when the ammoxidation catalyst composition comprises:

[A] at least one kind of oxides of vanadium and tungsten, and

[B]
  (1) at least one kind of oxides of antimony, phosphorus and boron, and/or
  (2) at least one kind of oxides of chromium, nickel, aluminum and silicon is used as an active component, fumaronitrile and maleonitrile are produced in high yields and the above-mentioned problems are successfully solved altogether.

That is to say, the present invention relates to a process for producing unsaturated aliphatic dinitriles which comprises reacting a gaseous straight-chain hydrocarbon having 4 carbon atoms with ammonia and oxygen in the presence of an ammoxidation catalyst composition containing as active components:

[A] at least one kind of oxides of vanadium and tungsten, and

[B]
  (1) at least one kind of oxides of antimony, phosphorus and boron, and/or
  (2) at least one kind of oxides of chromium, nickel, aluminum and silicon.

The catalyst which is used in the present invention contains, as the active component, mixed oxides or compound oxides of the elements as indicated in the above [A] and [B] (1) and (2). Ordinarily the active component is used in the state of being supported on a catalyst carrier, but this is not always required. The catalyst which is useful in the present invention is obtained by the per se known procedures of preparing solid catalyst, and can be prepared for example in the following manner:

Thus, the catalyst can be prepared by dissolving a vanadium-containing compound or a tungsten-containing compound, antimony-, phosphorus- or boron-containing compounds and/or chromium-, nickel-, aluminum- or silicon-containing compounds which can all be converted into oxides by chemical reaction or heating, in an appropriate solvent such as water, alcohols, acids and alkalis, if necessary, and then allowing them to be impregnated or deposited on a support, followed by calcination at temperature ranging from 300° to 800° C.

As the above-mentioned tungsten-containing compound, there may be mentioned tungsten oxide, ammonium tungstate, tungsten halides ($WCl_4$, $WCl_6$, $WO_2Cl_2$, $WBr_5$, etc.), heteropolyacids of tungsten (phosphotungstic acid, silicotungstic acid, borotungstic acid, their ammonium salts, etc.) and others, the vanadium-containing compound includes oxides of vanadium ($V_2O_5$, $V_2O_4$, $V_2O_3$, etc.), vanadic acid salts (ammonium vanadate, vanadyl oxalate, vanadyl sulfate, vanadyl tartarate, etc.), etc; the antimony-containing compound may be mentioned by oxides of antimony ($Sb_2O_3$, $Sb_2O_4$, $Sb_2O_5$), antimonic acids (orthoantimonic acid, metaantimonic acid, etc.), antimony halides and their partial hydrolysis products ($SbCl_3$, $SbCl_5$, $SbBr_3$, antimony oxychloride, etc.), organic antimony compounds (antimony triisopropoxide, etc.), antimony salts (antimony sulfide, antimony nitrate, tartar emetic, etc.), antimonates (potassium antimonate, etc.), and the like; as the phosphorus-containing compound, there may be mentioned phosphorus oxides ($P_2O_5$, $P_2O_3$, etc.), phosphoric acids ($HPO_3$, $H_3PO_4$, $H_4P_2O_7$, etc.), phosphoric acid salts (($NH_4)_3PO_3$, $(NH_4)_2HPO_4$, $BPO_4$, etc.), halides ($PCl_3$, $PCl_5$, $POCl_3$, $PBr_5$, etc.) and the like; the boron-containing compound includes boron oxide, boric acid, halides ($BCl_3$, $BF_3$, etc.), and others; as the chromium-containing compound, there may be mentioned oxides of chromium (CrO, $Cr_2O_3$, $CrO_3$), ammonium chromate, salts of chromium (chromium nitrate, chromium chloride, chromium oxalate, chromium tartarate, chromium sulfate, etc.), and others; as the nickel-containing compound, there may be mentioned nickel oxides (NiO, $Ni_2O_3$, etc.), nickel hydroxides ($Ni(OH)_2$, $Ni(OH)_3$, etc.), salts of nickel (nickel nitrate, nickel chloride, nickel sulfate, nickel formate, nickel acetate, nickel oxalate, etc.) and others; the aluminum-containing compound includes aluminum oxide, aluminum hydroxide, salts of aluminum (aluminum nitrate, aluminum chloride, aluminum sulfate, aluminum acetate, etc.), organic aluminum compounds (aluminum isopropoxide, etc.) and others; and the silicon-containing compound includes silicon oxide, silicic acids ($H_2SiO_3$, $H_4SiO_4$, etc.), halides ($SiCl_4$, etc.), silicon-containing heteropolyacids (silicotungstic acid, etc.) and others, whereby the compounds exemplified above are all easily convertible to oxides.

Preparation of the catalyst composition which is used in the present invention can be achieved with use of the above-mentioned various element containing compounds as raw materials by the means of the per se known methods for preparing catalyst such as coprecipitation method, impregnating method, kneading method and oxide mixing method.

In such case;

(1) The elements of tungsten and vanadium in [A] may be each contained solely, but when both elements are contained in combination, the mixing proportion of vanadium to tungsten is 0.01 to 100, preferably 0.1 to 10, more preferably 0.1 to 5 based on the atom ratio of each element.

(2) At least one element of antimony, phosphorus and boron as described in [B](1) and/or at least one element of chromium, nickel, aluminum and silicon as described in [B](2) are added to at least one element of tungsten and vanadium as described in [A] in the proportion of 0.001 to 100, preferably 0.01 to 50, more preferably 0.03 to 25 atoms per atom of the element of [A].

In cases in which the element as described in [B](1) is used as a mixture with the element as described in [B](2), the mixing proportion of both elements can be entirely arbitrary. The component of [B](1) acts to enhance the selectivity for dinitriles, whereas the component of [B](2), though it is effective in enhancing the selectivity, has the effect of increasing the activity and lowering the reaction temperature.

As the above support, preferred use is made of heat-resistant inorganic compounds such as alumina, silicon carbide, titanium oxide, silica magnesia, diatomaceous earth, pumice, zirconium oxide, cerium oxide, calcium sulfate, titanium phosphate, silicon phosphate and their mixtures. Among others, alumina, titanium oxide and titanium phosphate are particularly preferable. The amount of the active component to the total weight of the catalyst varies depending upon the used support, method of preparing the catalyst, atom ratio of the active component, etc., but is generally 2 to 90 weight %, preferably 5 to 70 weight %.

As the more specific preparation method for the catalyst which is used in the present invention, there may be mentioned, by way of example, the procedure which comprises adding to a mixed solution of an aqueous solution of silicotungstic acid and an aqueous oxalic acid solution of vanadium pentaoxide first aqueous solutions of chromium trioxide and phosphoric acid and then a molded or powdered support, evaporating the mixture to dryness over a water bath and calcining it at temperatures in the range of 500° C.

As the straight-chain hydrocarbon which is useful as a raw material in the present invention, there may be mentioned n-butane, 1-butene, cis-2-butene, trans-2-butene, butadiene-1,3, BB fraction, spent BB fraction, spent-spent BB fraction, etc. As the oxygen-containing gas, air is normally used, but use may also be made of oxygen or a mixture of oxygen and air, a mixture of air and carbon dioxide, a mixture of air and steam, and a mixture of air and nitrogen. The reaction temperature varies widely with the type and mixing ratio of raw material gases, catalyst composition, support, etc., and is normally ranging from 300° to 650° C., particularly preferably 400° to 600° C. Usually, but not always, increasing reaction temperature tends to increase the yield of the desired dinitriles. The mixing ratio of a $C_4$ hydrocarbon to ammonia used and oxygen can be arbitrary. But the mole ratio of a $C_4$ compound for each mole of ammonia may preferably be not less than the stoichiometric ratio. For example, the mole ratio of $C_4$ compound:ammonia:air is 0.1 to 10:0.2 to 50:40 to 99.7. The raw material gas is desirably contacted with the catalyst normally at space velocities (as converted to NTP) in the range of 300 to 30,000 ($hr^{-1}$), preferably 1,000 to 10,000 ($hr^{-1}$).

Unreacted $C_4$ compounds and ammonia may be used by recyclization.

The produced dinitriles, after being collected directly as solids or as liquids by cooling or by absorbing in suitable solvents, do not require any particular purification, but can be made the dinitriles with higher degrees of purity by the means of distillation, etc.

In the following Examples, "part" and "parts" mean "weight part" and "weight parts" unless otherwise stated.

EXAMPLE 1

In 100 parts of water was suspended 13.1 parts of ammonium para-tungstate, and while the suspension was heated at about 100° C. over a hot-water bath, 10 parts of oxalic acid was added to prepare the uniform solution (a). 1.90 Parts of antimony trichloride dissolved in 10 parts of ethanol was subjected to hydrolysis to prepare the hydrogel of antimony hydroxide (b). To (a) were added 40 parts of finely powdered titanium oxide calcined at 800° C. as a support and (b), and the mixture was made slurry by evaporating part of water with adequate stirring over a hot-water bath, followed by the wet-molding to a shape of 2 mm diameter by 5 mm length. The moldings were dried overnight at 100° C., and calcined in the air at 500° C. for 4 hours, thus yielding a catalyst.

10 ml of the catalyst thus prepared was packed into a flow-type fixed-catalyst bed reactor with 13 mm of inner diameter having a fluidized heating bath, and a mixed gas of 1 mole% of butadiene, 5 mole% of ammonia and 94 mole% of air was fed at atmospheric pressure at a space velocity of 2000 ($hr^{-1}$) (as converted to NTP) to conduct the ammoxidation reaction. The yield of fumaronitrile and maleonitrile (hereinafter referred to briefly as "yield of FN+MN") at 497° C. was 23.0 mole% based on butadiene fed.

Separation and quantitative determination of fumaronitrile and maleonitrile were carried out by use of a gas chromatograph, and the yield of the dinitriles was calculated. Further, these dinitriles were identified as fumaronitrile and maleonitrile by means of elemental analysis, infrared spectrophotometry, GC-MASS analysis, etc.

EXAMPLE 2

Four parts of phosphotungstic acid was dissolved in 40 parts of water. To the solution was added 3 parts of oxalic acid. While the mixture was heated at about 100° C. on a hot-water bath, 30 parts of finely powdered titanium oxide was added thereto. Subsequently, the same procedure as in Example 1 was conducted to prepare a catalyst. The reaction carried out in the same condition as in Example 1 yields FN+MN at 497° C. with 15.8 mole% based on butadiene fed.

EXAMPLE 3

A catalyst was prepared by the same procedure as in Example 1, except that a solution of 3.11 parts of boric acid in 20 parts of water was used in place of the hydrogel of antimony hydroxide used in the preparation of the catalyst of Example 1.

The reaction was carried out in the same reaction conditions as in Example 1, except that the space velocity in the reaction conditions of Example 1 was changed to 1500 (hr$^{-1}$), and the yield of FN+MN at 580° C. was 36.4 mole%.

EXAMPLE 4

A catalyst was prepared by the same procedure as in Example 1, except that a solution of 5 parts of chromium trioxide in 20 parts of water was used in place of (b) of Example 1.

The reaction was carried out in the same conditions as in Example 1, and the yield of FN+MN at 472° C. was 13.8 mole%.

EXAMPLE 5

To (a) of Example 1 was added a solution of 14.6 parts of nickel nitrate in 50 parts of water, and 40 parts of finely powdered alumina calcined at 1200° C. was used as a support. Subsequently, the same procedure as in Example 1 was conducted to prepare a catalyst.

The reaction carried out in the same conditions as in Example 1 yields FN+MN at 521° C. with 26.9 mole%.

EXAMPLE 6

A catalyst was prepared by the same procedure as in Example 1, except that a solution of 18.8 parts of aluminum nitrate in 20 parts of water was used in place of (b) of Example 1.

The reaction carried out in the same conditions as in Example 1 yields FN+MN at 573° C. with 33.1 mole%.

EXAMPLE 7

To a solution of 2.38 parts of silicotungstic acid and 2 parts of oxalic acid in 30 parts of water was added 30 parts of finely powdered titanium oxide calcined at 800° C. as a support. Subsequently, the same procedure as in Example 1 was conducted to prepare a catalyst. The reaction was carried out in the same conditions as in Example 1, and as a result, the yield of FN+MN at 507° C. was 19.0 mole%.

EXAMPLE 8

A hydrogel of antimony hydroxide prepared by hydrolysis of an ethanol solution containing 2.28 parts of antimony trichloride and a solution of 5 parts of chromium trioxide in 20 parts of water were admixed with (a) of Example 1. To the mixture was added 40 parts of powdered titanium oxide as a support, and subsequently, the same procedure was conducted to prepare a catalyst.

The reaction carried out in the same conditions as in Example 1 yields FN+MN at 479° C. with 17.0 mole%.

EXAMPLE 9

A solution of 2.38 parts of silicotungstic acid and 2 parts of oxalic acid in 30 parts of water was mixed with a solution of 0.533 part of boric acid in 20 parts of water. To the mixture was added 30 parts of finely powdered titanium oxide as a support. Subsequently, the same procedure as in Example 1 was conducted to prepare a catalyst.

The reaction carried out in the same conditions as in Example 1 yields FN+MN at 573° C. with 40.0 mole%.

EXAMPLE 10

A catalyst was prepared by the same procedure as in Example 9, except that 0.533 part of boric acid in Example 9 was replaced with 0.863 part of chromium trioxide.

The reaction carried out in the same conditions as in Example 1 yields FN+MN at 502° C. with 15.1 mole%.

EXAMPLE 11

A catalyst was prepared by the same procedure as in Example 9, except that 0.533 part of boric acid in Example 9 was replaced with 1.25 parts of nickel nitrate.

The reaction carried out in the same conditions as in Example 1, except that the space velocity in the reaction conditions of Example 1 was changed to 1500 (hr$^{-1}$) yields FN+MN at 517° C. with 31.1 mole%.

EXAMPLE 12

A catalyst was prepared by the same procedure as in Example 9, except that 0.533 part of boric acid in Example 9 was replaced with 4.80 parts of phosphoric acid.

The reaction carried out in the same conditions as in Example 1 yields FN+MN at 523° C. with 38.7 mole%.

EXAMPLE 13

In 50 parts of water was suspended 0.785 part of vanadium pentaoxide, and 6.5 parts of oxalic acid was added to the suspension while it was heated at about 100° C. on a hot water bath. Thus, the uniform solution (c) was prepared. An ethanol solution containing 7.88 parts of antimony trichloride was hydrolyzed to prepare a hydrogel of antimony hydroxide (d). To (c) were added 30 parts of finely powdered titanium oxide as a support and (d), and the mixture was made slurry by evaporating part of water from it while stirring well on a hot-water bath, followed by the wet-molding to a shape of 2 mm diameter by 5 mm length. The moldings were dried overnight at 100° C., and calcined in the air at 500° C. for 4 hours, to give a catalyst.

The reaction carried out in the same conditions as in Example 1 yields FN+MN at 493° C. with 17.3 mole%.

EXAMPLE 14

A catalyst was prepared by the same procedure as in Example 13, except that a solution of 9.6 parts of phosphoric acid in 30 parts of water was used in place of (d) in Example 13.

The reaction carried out in the same conditions as in Example 1 yields FN+MN at 471° C. with 24.3 mole%.

EXAMPLE 15

A catalyst was prepared by the same procedure as in Example 13, except that a solution of 0.173 part of chromium trioxide in 20 parts of water was used in place of (d) in Example 13.

With use of the same reactor as in Example 1, a mixed gas consisting of 0.5 mole% of butadiene, 2.5 mole% of ammonia and 97 mole% of air was fed at atmospheric pressure at a space velocity of 3000 (hr$^{-1}$) (as converted to NTP) to allow the reaction to occur, resulting in the yield of FN+MN at 431° C. with 11.9 mole%.

EXAMPLE 16

A catalyst was prepared by the same procedure as in Example 13, except that a solution of 0.50 part of nickel nitrate in 20 parts of water was used in place of (d) in Example 13.

The reaction carried out in the same conditions as in Example 15 yields FN+MN at 442° C. with 13.1 mole%.

EXAMPLE 17

To (c) of Example 13 were added antimony hydroxide prepared by hydrolyzing an ethanol solution containing 15.7 parts of antimony trichloride and a solution of 0.6 part of phosphoric acid in 20 parts of water, and 30 parts of finely powdered titanium oxide as a support was added to the mixed solution. Subsequently, the same procedure as in Example 13 was conducted to prepare a catalyst.

The reaction carried out in the same conditions as in Example 1 yields FN+MN at 490° C. with 31.1 mole%.

When the reaction was carried out by the use of a mixed gas consisting of 1 mole% of butadiene, 3 mole% of ammonia and 96 mole% of air, the yield of FN+MN at 476° C. was 29.2 mole%.

EXAMPLE 18

A catalyst was prepared by the same procedure as in Example 17, except that 1.97 parts of antimony trichloride was used in place of 15.7 parts of antimony trichloride and 9.6 parts of phosphoric acid being used in place of 0.6 part of phosphoric acid in Example 17.

The reaction carried out in the same conditions as in Example 1 yields FN+MN at 487° C. with 34.1 mole%.

EXAMPLE 19

A catalyst was prepared by the same procedure as in Example 17, except that 11.8 parts of antimony trichloride was used in place of 15.7 parts of antimony trichloride, and 0.865 part of chromium trioxide being used in place of 0.6 part of phosphoric acid in Example 17.

The reaction carried out in the same conditions as in Example 1 yields FN+MN at 459° C. with 14.5 mole%.

EXAMPLE 20

In 70 parts of water were suspended 1.13 parts of ammonium para-tungstate and 0.393 part of vanadium pentaoxide. 5.5 Parts of oxalic acid was added to the suspension, followed by heating at about 100° C. on a hot-water bath to give a uniform mixed solution containing tungsten and vanadium (e). Antimony hydroxide (f) prepared by the hydrolysis of an ethanol solution containing 7.88 parts of antimony trichloride and 30 parts of finely powdered titanium oxide as a carrier were added to (e), and part of water was evaporated from the mixture while it was stirred on a hot water bath, followed by molding to a shape of 2 mm diameter by 5 mm length. The moldings were dried overnight at 100° C., and calcined in the air at 500° C. for 4 hours to give a catalyst.

The reaction conducted in the same conditions as in Example 1 yields FN+MN at 455° C. with 25.3 mole%.

EXAMPLE 21

A catalyst was prepared by the same procedure as in Example 20, except that a solution of 9.6 parts of phosphoric acid in 30 parts of water was used in place of (f) in Example 20.

The reaction carried out in the same conditions as in Example 1 yields FN+MN at 490° C. with 40 mole%.

EXAMPLE 22

A catalyst was prepared by the same procedure as in Example 20, except that a solution of antimony hydroxide prepared by the hydrolysis of 1.97 parts of antimony trichloride and 4.8 parts of phosphoric acid in 30 parts of water was used in place of (f) in Example 20.

The reaction carried out in the same conditions as in Example 1 yields FN+MN at 500° C. with 41.6 mole%.

EXAMPLE 23

A 30-parts portion of spherical-formed alumina support of 3 mm diameter was soaked in a mixture of (e) of Example 20 and a solution of 0.173 part of chromium trioxide in 10 parts of water, and water was evaporated from it while heating on a hot water bath to thereby have the tungsten, vanadium and chromium components on the support, which was dried overnight at 100° C. and calcined at 500° C. for 4 hours to prepare a catalyst.

The reaction carried out in the same conditions as in Example 15 yields FN+MN at 452° C. with 13.1 mole%.

EXAMPLE 24

A catalyst was prepared by the same procedure as in Example 20, except that a solution of 1.25 parts of nickel nitrate in 20 parts of water was used in place of (f) in Example 20.

The reaction carried out in the same manner as in Example 15 yields FN+MN at 489° C. with 22.8 mole%.

EXAMPLE 25

A catalyst was prepared by the same procedure as in Example 20, except that a solution of antimony hydroxide prepared by the hydrolysis of 15.8 parts of antimony trichloride and 0.173 part of chromium trioxide in 10 parts of water was used in place of (f) in Example 20.

The reaction carried out in the same conditions as in Example 1 yields FN+MN at 498° C. with 15.5 mole%.

EXAMPLE 26

A catalyst was prepared by the same procedure as in Example 20, except that a solution of 9.6 parts of phosphoric acid and 0.432 part of chromium trioxide in 30 parts of water was used in place of (f) of Example 20.

The reaction carried out in the same conditions as in Example 1 yields FN+MN at 545° C. with 52.2 mole%.

EXAMPLE 27

A catalyst was prepared by the same procedure as in Example 20, except that a solution of 9.6 parts of phosphoric acid and 3.24 parts of aluminium nitrate in 30 parts of water was used in place of (f) of Example 20.

The reaction carried out in the same conditions as in Example 1 yields FN+MN at 481° C. with 41.3 mole%.

EXAMPLE 28

To 40 parts of water were added 1.19 parts of silicotungstic acid, 0.393 part of vanadium pentaoxide and 3.5 parts of oxalic acid, and the mixture was heated to about 100° C. on a hot-water bath to thus prepare a uniformly mixed solution containing tungsten, silicon and vanadium (g). A solution of 9.6 parts of phosphoric acid in 30 parts of water and 30 parts of powdered titanium oxide as a support were added to the solution, and subsequently, the same procedure as in Example 20 was conducted to prepare a catalyst.

The reaction carried out in the same conditions as in Example 1, except that the space velocity in the reaction conditions of Example 1 was changed to 3000 ($hr^{-1}$), yields FN+MN at 485° C. with 36.3 mole%.

EXAMPLE 29

A 30 parts portion of spherical-formed titanium oxide support of 3 mm diameter was soaked in a mixture of (g) of Example 28 and a solution of 5.35 parts of boric acid in 30 parts of water, and water was evaporated while the mixture was heated on a hot water bath to thus have the tungsten, vanadium, silicon and boron components on the support, which was dried overnight at 100° C., and calcined at 500° C. for 4 hours to prepare a catalyst.

The reaction carried out in the same conditions as in Example 1 yields FN+MN at 523° C. with 30.3 mole%.

EXAMPLE 30

To (g) of Example 28 were added a solution of 9.6 parts of phosphoric acid and 0.432 part of chromium trioxide in 30 parts of water and 30 parts of powdered titanium oxide as a support. The same procedure as in Example 20 was conducted to prepare a catalyst.

With use of the same reactor as in Example 1, a mixed gas consisting of 1 mole% of butadiene, 5 mole% of ammonia and 94 mole% of air was fed at atmospheric pressure at a space velocity of 2000 ($hr^{-1}$), whereby the yield of FN+MN at 552° C. was 49.3 mole%. In the case of the mixed gas being fed at a space velocity of 1500 ($hr^{-1}$), the yield of FN+MN at 560° C. was 56.2 mole%. When a mixed gas consisting of 0.5 mole% of butadiene, 2.5 mole% of ammonia and 97 mole% of air was fed at a space velocity of 3000 ($hr^{-1}$), the yield of FN+MN at 560° C. was 66.8 mole%.

EXAMPLE 31

The catalyst of Example 30 was packed into the reactor as used in Example 1, and a mixed gas consisting of 1 mole% of butene-1, 5 mole% of ammonia and 94 mole% of air was fed at a space velocity of 1500 ($hr^{-1}$), whereby the yield of FN+MN at 533° C. was 52.3 mole% based on butene-1 fed. When a mixed gas consisting of 0.7 mole% of butene-1, 2.6 mole% of ammonia and 96.7 mole% of air was fed at a space velocity of 3000 ($hr^{-1}$), the yield of FN+MN at 531° C. was 56.8 mole% based on butene-1 fed. In the case of a mixed gas of 1 mole% of cis-butene-2, 5 mole% of ammonia and 94 mole% of air being fed at a space velocity of 1500 ($hr^{-1}$), the yield of FN+MN at 535° C. was 53.7 mole% based on cis-butene-2 fed.

EXAMPLE 32

A catalyst was prepared by the same procedure as in Example 30, except that 1.25 parts of nickel nitrate was used in place of 0.432 part of chromium trioxide in Example 30.

With use of the same reactor as in Example 1, a mixed gas consisting of 1 mole% of butadiene, 5 mole% of ammonia and 94 mole% of air was fed at a space velocity of 2000 ($hr^{-1}$), whereby the yield of FN+MN at 503° C. was 47.7 mole%. In the case of a mixed gas of 0.5 mole% of butadiene, 2.5 mole% of ammonia and 97 mole% of air being fed at a space velocity of 3000 ($hr^{-1}$), the yield of FN+MN at 498° C. was 60.7 mole%.

EXAMPLE 33

The catalyst of Example 32 was packed into the reactor as used in Example 1, and a mixed gas consisting of 0.5 mole% of n-butane, 2.5 mole% of ammonia and 97 mole% of air was fed at a space velocity of 3000 ($hr^{-1}$), whereby the yield of FN+MN at 598° C. was 46.0 mole% based on the reacted n-butane, and the conversion of n-butane was 57.0 mole%.

EXAMPLE 34

To 40 parts of water were added 1.43 parts of tungstic acid, 0.314 part of vanadium pentaoxide and 3.5 parts of oxalic acid, and the mixture was heated at about 100° C. over a hot-water bath, thus preparing a uniform solution (g') having the mixing ratio of tungsten, vanadium and silicon different from the one in Example 28. Subsequently, the same procedure as in Example 28 was carried out and a catalyst was prepared.

The reaction was carried out in the same conditions as in Example 1. The yield of FN+MN at 525° C. was 48.0 mole%.

We claim:

1. In a process for producing fumaronitrile and maleonitrile which comprises reacting at least one straight chain hydrocarbon having 4 carbon atoms with ammonia and oxygen in the presence of an ammoxidation catalyst composition, the improvement wherein the ammoxidation catalyst consists essentially of the following active components:
   (A) at least one oxide of vanadium and tungsten, and
   (B)
   (1) at least one oxide of antimony, phosphorus and boron, and/or
   (2) at least one oxide of chromium, nickel, aluminum and silicon.

2. A process as claimed in claim 1 wherein the catalyst composition contains the active components of [A] and [B] in the proportion of 0.001 to 100 atoms of the element of [B] per atom of the element of [A].

3. A process as claimed in claim 1 wherein the catalyst composition contains the active components of [A] and [B] in the proportion of 0.01 to 50 atoms of the element of [B] per atom of the element of [A].

4. A process as claimed in claim 1 wherein the catalyst composition contains the active components of [A] and [B] in the proportion of 0.03 to 25 atoms of the element of [B] per atom of the element of [A].

5. A process as claimed in claim 1 wherein the catalyst composition contains 2 to 90% of the active components based on the total weight of the catalyst composition.

6. A process as claimed in claim 1 wherein the active components are supported on alumina, titanium oxide or titanium phosphate.

7. A process as claimed in claim 1 wherein the straight-chain hydrocarbon having 4 carbon atoms is at least one hydrocarbon selected from the group consisting of n-butane, 1-butene, cis-2-butene, trans-2-butene, and butadiene-1,3.

* * * * *